（12）United States Patent
Kotar Jordan et al.

(10) Patent No.: US 7,745,429 B2
(45) Date of Patent: Jun. 29, 2010

(54) CRYSTAL FORMS OF OLANZAPINE AND PROCESSES FOR THEIR PREPARATION

(75) Inventors: Berta Kotar Jordan, Kostanjevica na Krki (SI); Franc Vrecer, Straza pri Novem mestu (SI); Marija Grcman, Velika Loka (SI)

(73) Assignee: KRKA, D.D. Novo Mesto, Novo mesto (SI)

( * ) Notice: Subject to any disclaimer, the term of this patent is extended or adjusted under 35 U.S.C. 154(b) by 564 days.

(21) Appl. No.: 10/521,646

(22) PCT Filed: Jul. 14, 2003

(86) PCT No.: PCT/SI03/00024

§ 371 (c)(1),
(2), (4) Date: Jan. 13, 2005

(87) PCT Pub. No.: WO2004/006933

PCT Pub. Date: Jan. 22, 2004

(65) Prior Publication Data

US 2006/0040920 A1 Feb. 23, 2006

(30) Foreign Application Priority Data

Jul. 15, 2002 (SI) .............................. P-200200175

(51) Int. Cl.
*A61K 31/551* (2006.01)
*A61P 25/00* (2006.01)
*C07D 495/04* (2006.01)

(52) U.S. Cl. ...................................... 514/220; 540/557
(58) Field of Classification Search ................. 514/220; 540/557
See application file for complete search history.

(56) References Cited

U.S. PATENT DOCUMENTS

| 5,229,382 | A | | 7/1993 | Chakrabarti et al. | ......... 514/220 |
| 5,703,232 | A | * | 12/1997 | Bunnell et al. | ............... 540/557 |
| 5,776,928 | A | * | 7/1998 | Beasley, Jr. | .................. 514/220 |
| 6,432,943 | B1 | * | 8/2002 | Tran | ........................... 514/220 |
| 6,506,746 | B2 | * | 1/2003 | Beasley, Jr. | .................. 514/220 |
| 6,780,433 | B2 | * | 8/2004 | Cochran et al. | ............. 424/480 |
| 7,229,643 | B2 | * | 6/2007 | Cochran et al. | ............. 424/480 |

FOREIGN PATENT DOCUMENTS

| EP | 0 733 634 | 9/1996 |
| EP | 0 733 635 | 8/2001 |
| EP | 0 831 098 | 11/2001 |
| EP | 0 831 097 | 7/2002 |
| WO | WO 01/47933 | 7/2001 |
| WO | WO 02/18390 | 3/2002 |

\* cited by examiner

*Primary Examiner*—Brenda L Coleman
(74) *Attorney, Agent, or Firm*—Cohen Pontani Lieberman & Pavane LLP

(57) ABSTRACT

The invention relates to a process for the preparation of form I of olanzapine, crystallized from a solvent mixture which comprises 2-propanol, some pseudopolymorphic forms, namely solvates of olanzapine, a new polymorphic form A of olanzapine, and processes for the preparation thereof.

23 Claims, 6 Drawing Sheets

US 7,745,429 B2

CRYSTAL FORMS OF OLANZAPINE AND PROCESSES FOR THEIR PREPARATION

PRIORITY CLAIM

This is a U.S. national stage of application No. PCT/SI03/00024, filed on Jul. 14, 2003. Priority is claimed on that application and on the following application Country: Slovenia, Application No.: P-200200175, Filed: Jul. 15, 2002.

TEHCHNICAL FIELD

The present invention belongs to the field of organic chemistry and relates to a new polymorphic form A of 2-methyl-4-(4-methyl-1-piperazinyl)-10H-thieno [2,3-b] [1,5] benzodiazepine (hereinafter referred to by its generic name "olanzapine") and some pseudopolymorphic forms, namely solvates of olanzapine, a method for production thereof and a method for preparation of polymorphic form I of olanzapine.

Olanzapine has shown to have activity with regard to the central nervous system and is also useful for the treatment of schizophrenia, schizophreniform disorders, acute mania, mild anxiety states and psychosis.

TECHNICAL PROBLEM

According to prior art processes, solvents, like methylene chloride and acetonitrile, are used for the crystallization of form I of olanzapine. However, these solvents are not recommended for use in the preparation of pharmaceutical products, as they are harmful. Moreover, halogenated solvents such as methylene chloride are not environmentally friendly and therefore their use should be limited. Finally, olanzapine is highly soluble in methylene chloride and therefore the yields are not satisfactory for large-scale industrial production.

Moreover, the prior art processes often do not lead to satisfactory yields of the form I of olanzapine.

Consequently, there is a need for an improved process to prepare form I of olanzapine.

Further, there is a need for precursors which allow the easy preparation of polymorphic forms of olanzapine or the conversion to other forms of olanzapine.

These problems are solved by the present invention.

The invention also relates to a new polymorphic form of olanzapine which is designated "form A of olanzapine", a process for its preparation as well as pharmaceutical compositions comprising it.

BACKGROUND OF THE INVENTION

The British patent GB 1 533 235 discloses antipsychotically effective thienobenzodiazepines by a generic formula which also covers olanzapine.

U.S. Pat. No. 5,229,382 describes olanzapine explicitly. The described process for its production involves a crystallization from acetonitrile, determining the melting point of that crystallized compound at 195° C.

EP-B-733 635 claims crystalline form II olanzapine and this polymorphic form is said to be more stable than the material obtained according to U.S. Pat. No. 5,229,382 which is designated "form I olanzapine". Both the form I and the form II of olanzapine are characterized by e.g. x-ray data. The preparation of the more stable form II of olanzapine is effected by dissolving technical grade olanzapine in ethyl acetate and crystallization from the resulting solution by any conventional process such as seeding, cooling, scratching the glass of the reaction vessel or other common techniques.

WO 02/18390 discloses the monohydrate form I and the dihydrate form I of olanzapine, a process for production thereof and a process for production of form I of olanzapine which comprises the steps of stirring olanzapine monohydrate form I or crude olanzapine or form II of olanzapine in methylene chloride at reflux, cooling, filtering and drying. It is also described that a repeating of the process described in U.S. Pat. No. 5,229,382 Example 1, subexample 4 did not lead to formation of form I of olanzapine.

EP-B-733 634 relates to three specific solvates of olanzapine namely the methanol, ethanol and 1-propanol solvates and a process for production technical grade olanzapine by drying the corresponding solvate.

EP-B-831 098 relates to processes for preparation of form II of olanzapine by drying olanzapine dihydrate intermediates in a vacuum oven.

EP-A-831 097 relates to olanzapine dihydrate D.

In WO 01/47933 three new polymorphic forms designated as form III, IV and V and methods for preparing them are disclosed. The processes involve a dissolving of form I or form II of olanzapine in aqueous organic or anorganic acid and precipitating the desired material by neutralisation.

US patent application 20020086993 discloses new polymorphic form designated as form X of olanzapine and a method for its preparation.

DETAILED DESCRIPTION OF THE INVENTION

Figure 1:
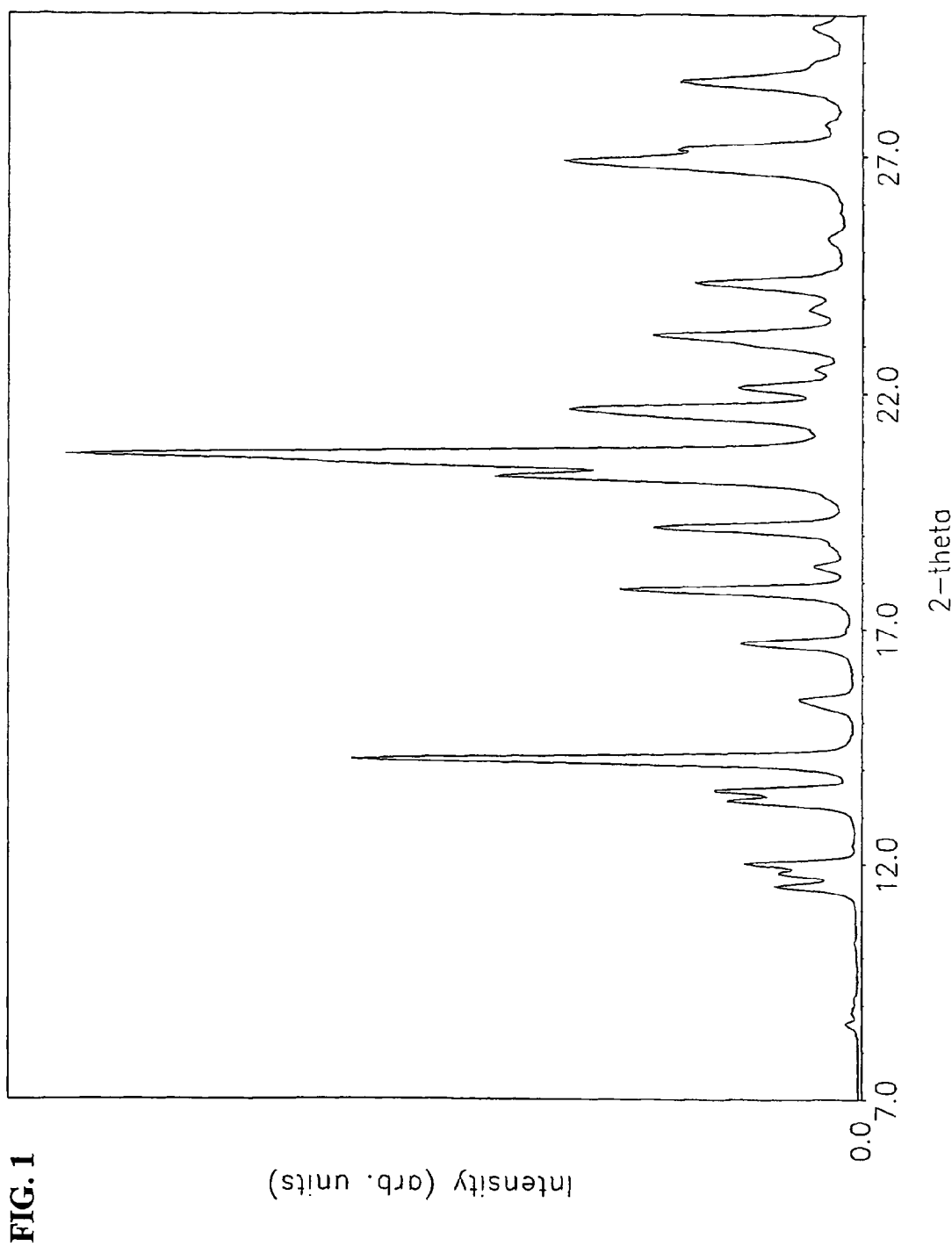
FIG. 1 shows the powder x-ray diffraction pattern of form A of olanzapine
Figure 2:
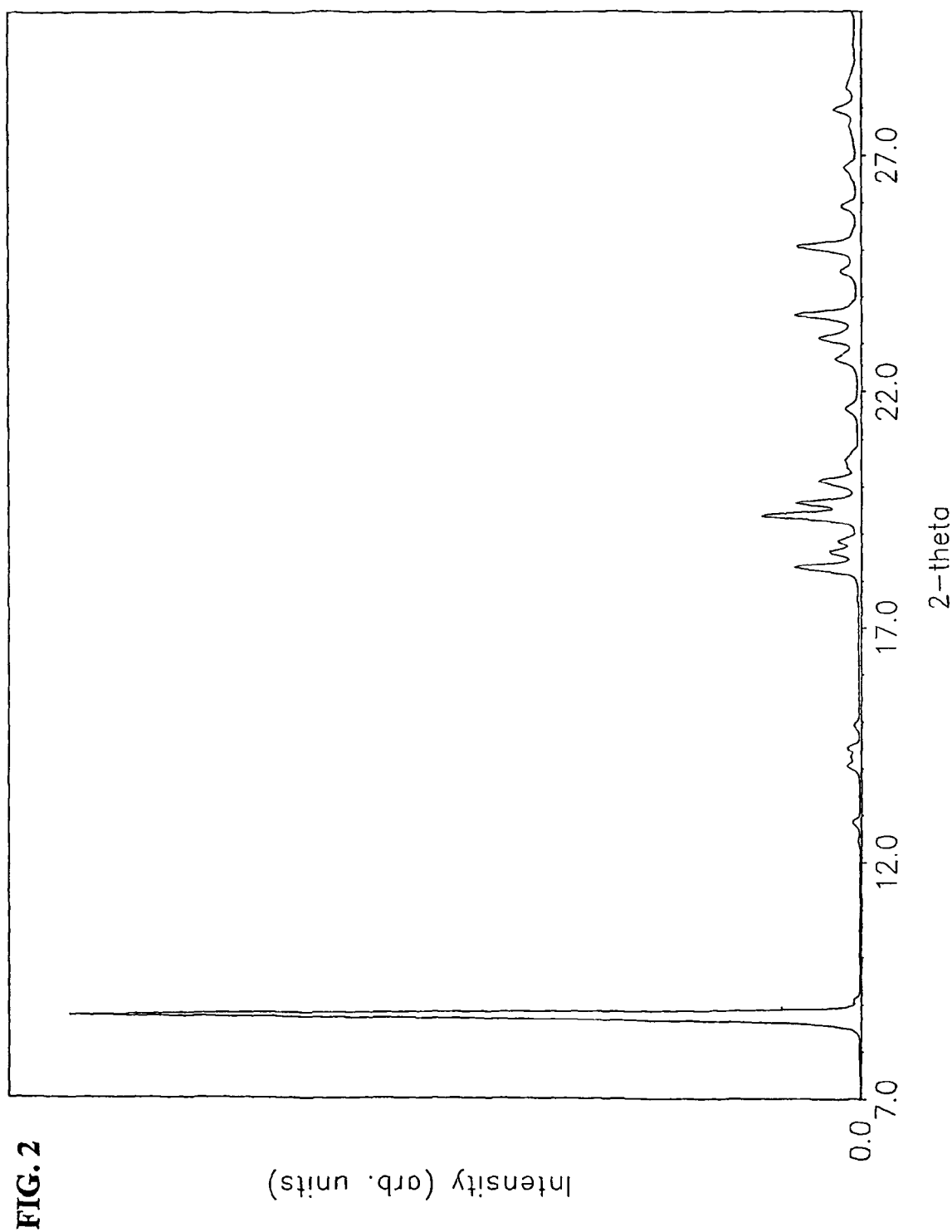
FIG. 2 shows the powder x-ray diffraction pattern of olanzapine acetonitrile/methylene chloride/water mixed solvate
Figure 3:
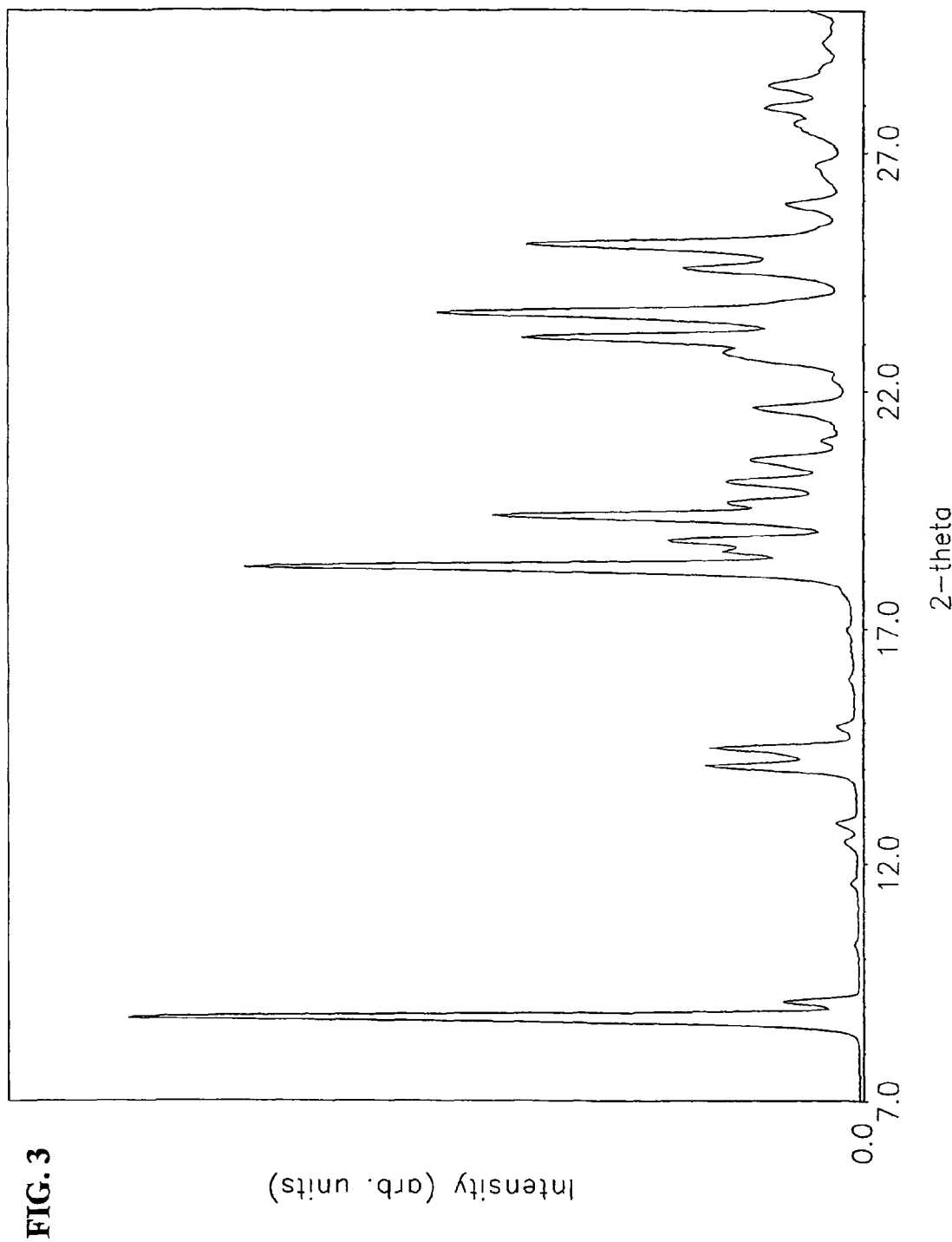
FIG. 3 shows the powder x-ray diffraction pattern of olanzapine acetonitrile/water mixed solvate
Figure 4:
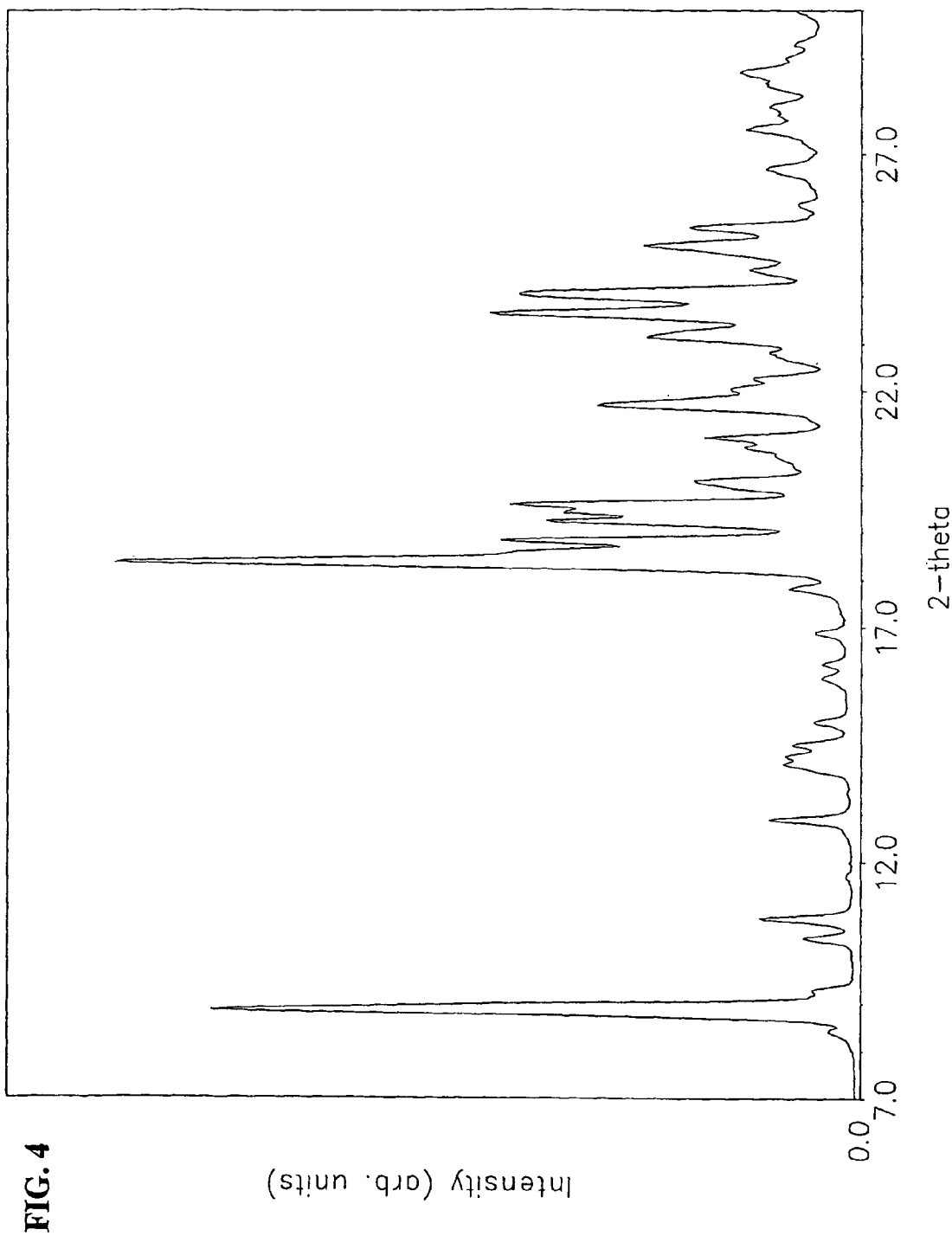
FIG. 4 shows the powder x-ray diffraction pattern of olanzapine methylene chloride IA solvate
Figure 5:
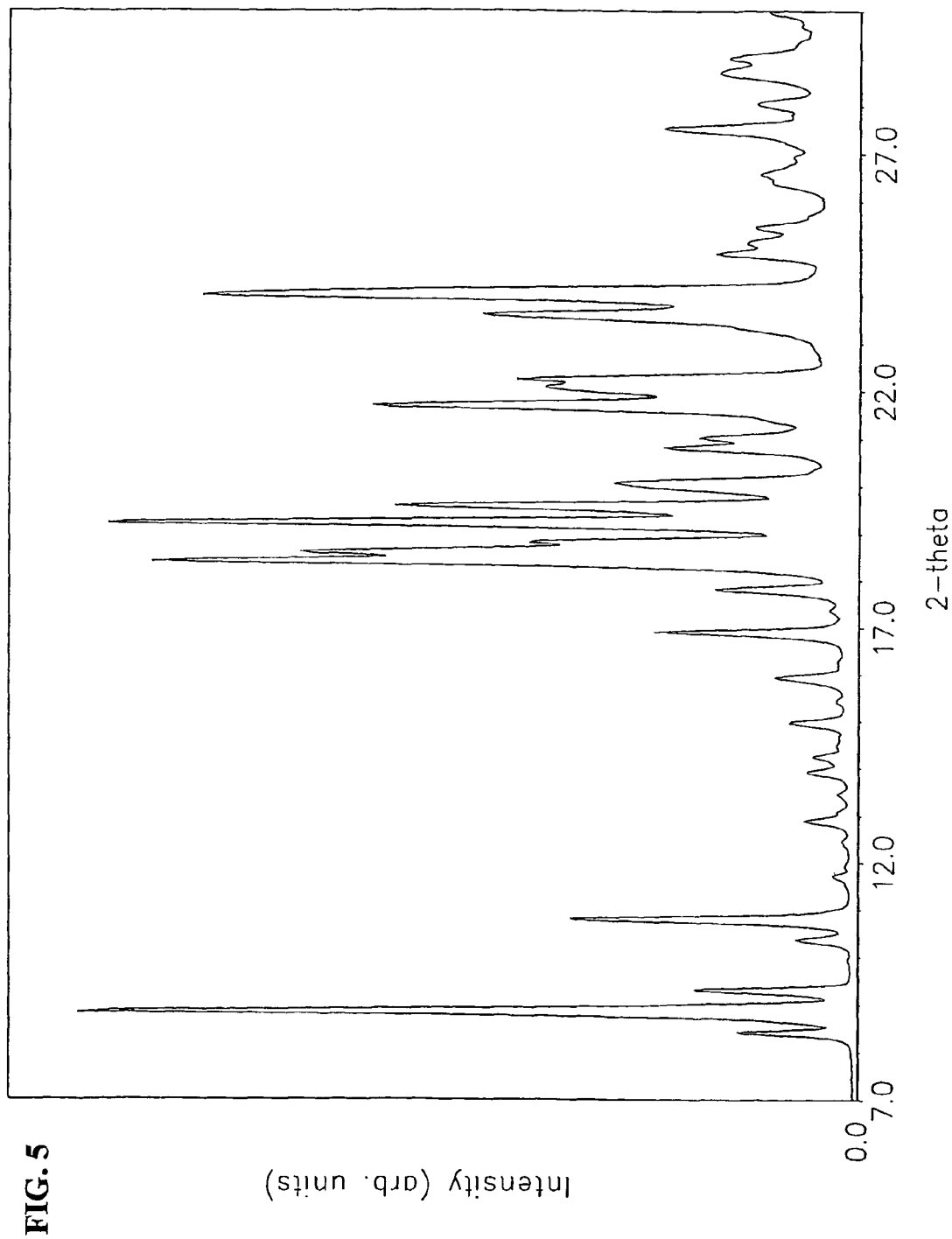
FIG. 5 shows the powder x-ray diffraction pattern of olanzapine methylene chloride IB solvate
Figure 6:
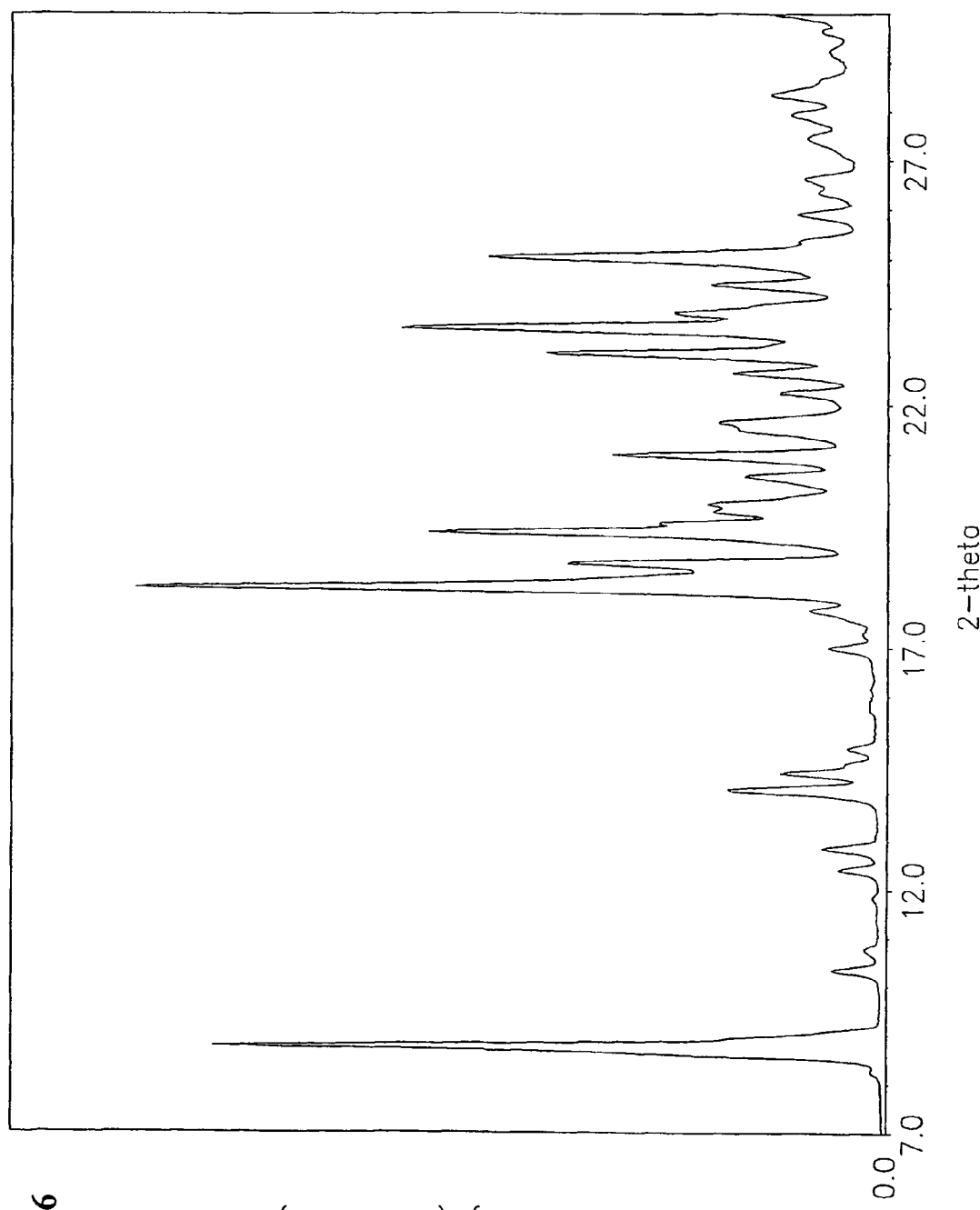
FIG. 6 shows the powder x-ray diffraction pattern of olanzapine 2-propanol solvate

It has unexpectedly been found that the preparation of form I of olanzapine can easily be accomplished if olanzapine is crystallized by using the non-harmful solvent mixture which comprises 2-propanol.

The process according to the invention for the preparation of form I of olanzapine is characterized by crystallization of olanzapine from the solvent 2-propanol or from a solvent mixture which comprises 2-propanol.

The solvent mixture also comprises at least one further solvent in which olanzapine is soluble and this further solvent is aprotic, in particular selected from the group consisting of tetrahydrofuran, methylene chloride, acetone, toluene, N,N-dimethylformamide, dimethylsulfoxide, and chloroform.

It is preferred that the solvent mixture comprises 2-propanol and the at least one further solvent in a ratio of 1:0.1 to 5 parts, more preferably 1:0.3 to 3 and most preferably 1:0.5 to 1.5 by volume.

The olanzapine used as a starting material can be in any form, e.g. it can be in reaction solution, crude or in anhydrous or solvated form. We have observed that in case a hydrate is used as olanzapine starting material or an aqueous solvent is employed, then formation of hydrates in the final product is very likely to occur. Since the product in form of hydrates is not desirable, it is preferred to avoid hydrates as starting material and aqueous solvents. The final form I of olanzapine obtained will therefore be preferably substantially free from hydrates. Form I of olanzapine obtained by the process of this invention contains preferably less than 0.5%, more preferably less than 0.2% and most preferably less than 0.1% by weight of associated water.

The process for preparing form I of olanzapine usually involves dissolving of olanzapine starting material in a solvent mixture which comprises 2-propanol, and then crystallizing and recovering the product by conventional processes.

In the following preferred embodiments of the process are described.

The process preferably involves a heating of the mixture of the olanzapine starting material and the solvent until a clear solution is obtained, in particular a heating to temperatures from 30° C. to the boiling point of the solvent, preferably from 50 to 55° C. After the clear solution is obtained, a part of the solvent is evaporated under vacuum at temperatures ranging from room temperature to 60° C., preferably at 30 to 35° C. It is preferred that the evaporated part of the solvent makes up 20 to 70%, based on the total volume of solvents. After evaporation, a seeding of the remaining solution with crystals of form I of olanzapine is conducted. Seeding with higher amounts of polymorph form I, such as for example 10%, increases the speed of crystallization. The product can then be isolated by conventional processes including further vacuum evaporation at the same temperature so that the total volume of the solvent is reduced by 30 to 90% or by cooling the solution to about room temperature, i.e. about 20° C. At temperatures below room temperature, the formation of solvates is favoured.

In a further preferred embodiment, the process according to the invention is carried out by using the olanzapine starting material in form of a solvate of olanzapine. Preferably, the solvate is at least one of the group consisting of a methylene chloride solvate, a 2-propanol solvate and an acetonitrile mixed solvates of olanzapine. The mixed solvates have incorporated acetonitrile and water (acetonitrile/water mixed solvate) or acetonitrile, methylene chloride and water (acetonitrile/methylene chloride/water mixed solvate).

When using a solvate of olanzapine as starting material, then it is preferred that the crystallisation of form I of olanzapine is performed at a temperature of 15 to 35° C., in particular at room temperature.

Form I of olanzapine is rather difficult to be prepared in substantially pure form, because formation of the thermodynamically more stable form II is favoured. However, by using the above crystallization conditions, it was possible to prepare form I of olanzapine with yields higher than 70%. According to the process of the present invention substantially pure form I free from form II and solvates could be obtained.

A further aspect of the present invention are specific solvates of olanzapine, a process for the preparation thereof and their use in the preparation of in particular anhydrous forms of form I of olanzapine.

We have found out that the 2-propanol solvate, the acetonitrile solvate and the methylene chloride solvate could be formed. The latter solvate was found to exist in two forms with different molar ratio between the olanzapine and methylene chloride.

Depending on the form, the solvates can be transformed to forms I, II, III, IV, V, X, to the new form A of olanzapine or to the mixture thereof, described hereinafter.

Powder x-ray diffraction patterns were measured on a Siemens D-5000 diffractometer with Cu Kα radiation, 2-theta range from 7 to 30 degree, step 0.034 degree 2-theta, divergent slit 20 mm and receiving slit 0.6 mm. The characteristic powder diffraction peaks are expressed in degrees 2-theta.

As used herein, the following abbreviated terms are: "vs" refers to very strong relative intesity up to 50%, "s" refers to strong relative intensity from 25 to 50%, "m" refers to medium relative intensity from 10 to 25%, "w" refers to weak relative intensity from 5 to 10% and "vw" refers to very weak relative intensity from 0 to 5%.

Infrared (FT-IR) spectra were obtained in a KBr disk using a Perkin Elmer FT-IR spectrometer Spectrum 1000 at resolution 4 cm$^{-1}$. The characteristic absorption bands are expressed in cm$^{-1}$.

The acetonitrile/methylene chloride/water mixed solvate is characterized by the following data:

Typical X-ray diffraction pattern is represented by following 2-theta degrees accompanied with intensities:

| 2-theta | int. |
| --- | --- |
| 8.76 | vs |
| 18.29 | w |
| 19.39 | m |
| 19.66 | w |
| 20.12 | w |
| 23.13 | w |
| 23.62 | w |
| 25.08 | w |

Preferably it is characterized by the following 2-theta degrees: 8.76, 19.39, 20.12.

IR spectra is characterised by the following characteristic peaks: 3430, 3236, 2933, 2844, 1592, 1560, 1468, 1458, 1409, 1366, 1341, 1297, 1282, 1265, 1220, 1149, 1004, 970, 850, 779, 754, 669 cm$^{-1}$.

The acetonitrile/methylene chloride/water mixed solvate is prepared by dissolving olanzapine in any form in a solvent mixture of acetonitrile and methylene chloride and by heating to a temperature of about 50° C. until a clear solution is obtained, cooling the solution to a temperature of below 10° C., and optionally removing a part of the solvents by evaporation in order to enhance yields.

The acetonitrile/methylene chloride/water mixed solvate can be converted to form A of olanzapine by removing the solvent by drying.

The acetonitrile/water mixed solvate of olanzapine according to the invention is characterized by the following data:

Typical X-ray diffraction pattern is represented by following 2-theta degrees accompanied with intensities:

| 2-theta | int. |
| --- | --- |
| 8.76 | vs |
| 9.10 | m |
| 14.05 | m |
| 14.44 | m |
| 18.30 | vs |
| 18.67 | m |
| 18.84 | s |
| 19.37 | s |
| 19.68 | m |
| 20.10 | m |
| 20.54 | m |

-continued

| 2-theta | int. |
|---|---|
| 21.65 | m |
| 22.79 | m |
| 23.12 | s |
| 23.62 | vs |
| 24.55 | m |
| 25.06 | s |
| 25.92 | m |
| 27.96 | m |
| 28.44 | m |

Preferably it is characterised by the following 2-theta degrees: 8.76, 9.10, 14.05, 19.37, 20.10, 24.55, 25.92, 27.96.

IR spectra is characterised by the following characteristic peaks: 3401, 3235, 2930, 2843, 1592, 1561, 1467, 1458, 1409, 1366, 1341, 1282, 1265, 1219, 1148, 1004, 970, 852, 779, 754, 668 $cm^{-1}$.

The acetonitrile/water mixed solvate is prepared by dissolving olanzapine in any form in acetonitrile or in a mixture of acetionitrile with aqueous ammonia, heating the mixture to a temperature from 30° C. to the boiling point to obtain a clear solution, cooling the solution, preferably to temperatures of from 10° C. to –30° C., or evaporating a part of the solvent, and isolating the product by conventional means.

This form of acetonitrile/water mixed solvate can, for example, be converted to form II of olanzapine by drying.

The 2-propanol solvate of olanzapine is characterized by the following data:

Typical X-ray diffraction pattern is represented by following 2-theta degrees accompanied with intensities:

| 2-theta | int. |
|---|---|
| 8.74 | vs |
| 14.05 | m |
| 14.41 | m |
| 17.77 | m |
| 18.22 | vs |
| 18.76 | s |
| 19.38 | vs |
| 19.81 | m |
| 19.95 | m |
| 20.54 | m |
| 20.96 | s |
| 21.64 | m |
| 22.26 | m |
| 22.65 | m |
| 23.03 | s |
| 23.58 | vs |
| 23.90 | s |
| 24.46 | m |
| 25.03 | vs |
| 25.39 | m |
| 25.92 | m |
| 26.63 | m |
| 27.47 | m |
| 27.95 | m |
| 28.36 | m |

Preferably it is characterized by the following 2-theta degrees: 8.74, 14.05, 19.38, 22.65, 23.03, 24.46, 25.92, 28.36.

IR spectra is characterized by the following characteristic peaks: 3400, 3234, 2962, 2931, 2843, 1590, 1559, 1468, 1413, 1282, 1267, 1220, 1147, 1004, 970, 846, 779, 756, 667 $cm^{-1}$.

The 2-propanol solvate of olanzapine according to the invention is prepared by suspending olanzapine in a mixture of 2-propanol and a further solvent in which olanzapine is soluble, such as tetrahydrofuran or methylene chloride, heating the mixture to obtain a clear solution, cooling the solution preferably to temperatures from 10° C. to –30° C., or evaporating a part of the solvent, and isolating the product by conventional processes.

The 2-propanol solvate can be converted to mixed form I and II of olanzapine by removing the solvent by drying.

Two methylene chloride solvates IA and IB of olanzapine according to the invention are characterised by the following spectra, the both forms can be in particular distinguished by IR spectra:

Form IA is characterized by the following data:

Typical X-ray diffraction pattern is represented by following 2-theta degrees accompanied with intensities:

| 2-theta | int. |
|---|---|
| 8.85 | vs |
| 10.80 | m |
| 12.89 | m |
| 14.09 | m |
| 14.25 | m |
| 18.37 | vs |
| 18.81 | s |
| 19.22 | s |
| 19.41 | s |
| 19.57 | s |
| 20.07 | m |
| 20.80 | m |
| 21.00 | m |
| 21.71 | s |
| 22.06 | m |
| 22.25 | m |
| 22.78 | m |
| 23.14 | s |
| 23.62 | s |
| 24.03 | s |
| 24.53 | m |
| 25.04 | s |
| 25.43 | m |
| 26.67 | m |
| 27.51 | m |
| 28.00 | m |
| 28.45 | m |
| 28.70 | m |

Preferably it is characterized by the following 2-theta degrees: 10.80, 14.25, 19.22, 22.78, 24.53.

IR spectra is characterized by the following characteristic peaks: 3435, 3237, 2918, 2842, 1590, 1560, 1467, 1413, 1366, 1343, 1282, 1266, 1219, 1147, 1004, 970, 846, 780, 757, 668 $cm^{-1}$.

Form IB is characterized by the following data:

Typical X-ray diffraction pattern is represented by following 2-theta degrees accompanied with intensities:

| 2-theta | int. |
|---|---|
| 8.43 | m |
| 8.86 | vs |
| 9.30 | m |
| 14.25 | m |
| 14.98 | m |
| 10.80 | s |
| 15.94 | m |
| 16.88 | s |
| 17.79 | m |
| 18.40 | vs |
| 18.57 | vs |

| 2-theta | int. |
|---|---|
| 18.83 | s |
| 19.23 | vs |
| 19.57 | vs |
| 20.04 | s |
| 20.79 | m |
| 21.01 | m |
| 21.68 | vs |
| 22.06 | s |
| 22.23 | s |
| 23.57 | s |
| 24.02 | vs |
| 24.89 | m |
| 25.12 | m |
| 25.46 | m |
| 26.38 | m |
| 26.56 | m |
| 27.50 | s |
| 28.06 | m |
| 28.71 | m |
| 29.02 | m |

Preferably it is characterized by the following 2-theta degrees: 9.30, 10.80, 14.25, 14.98, 15.94, 19.23, 20.04.

IR spectra is characterized by the following characteristic peaks: 3274, 2943, 2916, 2841, 1589, 1560, 1466, 1419, 1282, 1259, 1215, 1144, 1122, 1001, 970, 783, 759, 747, 725 cm$^{-1}$.

Both of methylene chloride solvates are prepared by dissolving olanzapine in methylene chloride, optionally with heating to obtain a clear solution. In case the solvent mixture is partly evaporated and cooled or completely evaporated, then form IB of methylene chloride solvate is obtained. In case the crystallisation mixture is rapidly cooled to temperatures about 0° C. form IA of methylene chloride solvate is obtained.

By drying and optionally compression or grinding of any one of methylene chloride solvate IA or IB, form I of olanzapine is obtained.

Generally, the aforementioned solvates according to the invention can be used for preparing other forms and in particular anhydrous forms of olanzapine. They are preferably used for preparing anhydrous olanzapine form I, II, III, IV, V, X, A or mixture thereof.

A further aspect of the invention is a new polymorphic form of olanzapine, designated as form A of olanzapine. This form A of olanzapine is characterized by the following data:
Typical X-ray diffraction pattern is represented by following 2-theta degrees accompanied with intensities:

| 2-theta | int. |
|---|---|
| 11.52 | m |
| 11.83 | m |
| 12.00 | m |
| 13.35 | m |
| 13.56 | m |
| 14.21 | vs |
| 15.47 | w |
| 16.69 | m |
| 17.83 | s |
| 19.16 | s |
| 20.25 | s |
| 20.69 | vs |
| 21.65 | s |
| 22.12 | m |
| 23.21 | s |
| 24.33 | m |
| 26.88 | s |
| 27.13 | m |
| 28.57 | m |

Preferably it is characterised by the following 2-theta degrees: 11.52, 12.00, 13.35, 13.56, 14.21, 15.47, 16.69, 19.16, 20.25, 20.69, 22.12, 24.33, 26.88, 27.13.

IR spectra is characterised by the following characteristic peaks: 3216, 2912, 2846, 2804, 1592, 1469, 1450, 1395, 1369, 1286, 1257, 1217, 1143, 1006, 964, 853, 752, 674 cm$^{-1}$.

The form A of olanzapine is prepared by suspending olanzapine in a mixture of acetonitrile with a solvent in which olanzapine is soluble or alternatively by dissolving olanzapine in a solvent where olanzapine is soluble, heating the mixture to obtain a clear solution, optionally filtration and partly evaporation of the solvent, and recovering the product by conventional procedures such as seeding, cooling, scratching the glass vessel or other common technique. The olanzapine used as starting material can be either crude olanzapine, olanzapine in any anhydrous form or any solvate form of olanzapine including the abovementioned solvates of acetonitrile, 2-propanol and methylene chloride according to the invention. Preferred solvents in which olanzapine is soluble are e.g. methylene chloride, tetrahydrofuran, acetone, toluene, N,N-dimethylformamide, dimethylsulfoxide and chloroform. The ratio of acetonitrile to other possible solvents is preferably 1:0.1 to 5 parts, preferably 1:0.1 to 3.0 and most preferred 1:0.2 to 1.5.

The mixture is usually heated to a temperature of from 30° C. to the boiling point of the mixture, preferably 40-60° C., to obtain the clear solution. It is further preferred to evaporate solvent from the clear solution under vacuum at temperatures ranging from 0° C. to 60° C., preferably 30 to 40° C. The evaporated part of the solvent should make up from 10 to 70% based on the total volume of solvents. Usually, the desired form A of olanzapine can be recovered by cooling or seeding of the solution with crystals of form A. The product can then be further dried in vacuum.

If the solution is rapidly cooled to temperatures under 5° C., then an acetonitrile/methylene chloride/water mixed solvate is usually formed. This solvate can, however, be transformed to form A of olanzapine by drying.

This new polymorphic form A is stable and therefore particularly suited for incorporation in pharmaceutical preparations. The invention therefore also relates to a pharmaceutical composition comprising form A of olanzapine.

The polymorphic form A of olanzapine can be formulated in a pharmaceutical composition in combination with one or more pharmaceutical acceptable excipients which can be either solid, semisolid or liquid. Pharmaceutical formulation can be prepared by any conventional techniques such as direct compression, dry and wet granulation, with or without final coating of the dosage form.

The final dosage form including form A of olanzapine can be in any conventional unit dosage forms such as granules, pellets, tablets, film coated tablets, fast dispersible tablets, capsules, suspensions and solutions for oral use, transdermal patches, suppositories, parenteral products, etc.

The invention is in the following further illustrated by examples.

EXAMPLES

Preparation of Form A of Olanzapine

Example 1

10.0 g of 2-methyl-4-(4-methyl-1-piperazinyl)-10H-thieno[2,3-b][1,5]benzodiazepine ("olanzapine") was suspended in a mixture of 50.0 ml methylene chloride and 50.0 ml acetonitrile. The obtained suspension was heated to 45 to 50° C. to obtain a clear solution. The solution was filtered and the solvent was evaporated under vacuum at 0 to 5° C. The product was recovered by vacuum filtration to obtain an acetonitrile/methylene chloride/water mixed solvate.

Upon drying under vacuum at 60° C., this solvate was converted to form A of olanzapine (8.94 g).

Example 2

10.0 g of 2-methyl-4-(4-methyl-1-piperazinyl)-10H-thieno[2,3-b][1,5]benzodiazepine ("olanzapine") was suspended in acetonitrile (30 ml). The suspension was heated to 50° C. and methylene chloride (35 ml) was added to obtain a clear solution. The methylene chloride was then evaporated under vacuum at 40° C. To the resulting solution a few seed crystals of form A of olanzapine were added and the mixture was stirred for one hour at 40° C. The product was filtered off and dried under vacuum at 60° C. to obtain form A of olanzapine (6.5 g).

Example 3

1.0 g of 2-methyl-4-(4-methyl-1-piperazinyl)-10H-thieno[2,3-b][1,5]benzodiazepine ("olanzapine") was suspended in acetonitrile (10 ml). The suspension was heated to 50° C. and toluene (2 ml) was added to obtain a clear solution. Approximately half of the solvent was evaporated under vacuum at 35 to 40° C., and then the remaining solution was seeded with the crystals of form A of olanzapine. The product was recovered by filtration and dried at 50° C. to obtain form A of olanzapine (0.76 g).

Example 4

1.0 g of 2-methyl-4-(4-methyl-1-piperazinyl)-10H-thieno[2,3-b][1,5]benzodiazepine ("olanzapine") was suspended in 6.0 ml of methylene chloride. The obtained suspension was heated to the boiling point to obtain a clear solution which was heated at this temperature for 3 hours. The solution was left at room temperature until the solvent evaporated. To the residue 6.0 ml of methylene chloride was added, the suspension was heated to 40° C., undissolved product was filtered and dried at room temperature to obtain olanzapine form A (0.4 g).

Preparation of Solvates

Acetonitrile/Water Mixed Solvate of Olanzapine

Example 5

10.0 g of 2-methyl-4-(4-methyl-1-piperazinyl)-10H-thieno[2,3-b][1,5]benzodiazepine ("olanzapine") was suspended in acetonitrile (110 ml), and the suspension was heated to reflux at a temperature of 82° C. The obtained clear solution was filtered hot. The filtrate was cooled to 0-5° C. and stirred under vacuum for 30 minutes. The product was isolated by vacuum filtration and dried under ambient conditions for 12 hours. Yield: 10.1 g.

Loss on drying (determined by TGA): 11.5%.
Assay of water (KF): 6.5%.
Molar ratio among olanzapine/acetonitrile/water (confirmed by $^1$H NMR analysis) is 1:½:1.

Example 6

5.0 g of 2-methyl-4-(4-methyl-1-piperazinyl)-10H-thieno[2,3-b][1,5]benzodiazepine ("olanzapine") was suspended in acetonitrile (210 ml), and the suspension was heated to 40° C. to obtain a clear solution. To this solution 2.4 ml 25% aqueous ammonia was added and the mixture was cooled to −30° C. within 20 minutes. The product was filtered and dried under vacuum for 1 hour at 50° C. Yield: 5.3 g.

Acetonitrile/Methylene Chloride/Water Mixed Solvate of Olanzapine

Example 7

1.0 g of 2-methy-4-(4-methyl-1-piperazinyl)-10H-thieno[2,3-b][1,5]benzodiazepine ("olanzapine") was suspended in a mixture of methylene chloride (5.0 ml) and acetonitrile (5.0 ml). The suspension was heated to 45-50° C. to obtain a clear solution. The solution was filtered and the solvent was evaporated under vacuum at 0-5° C. The product was recovered by vacuum filtration and dried under ambient conditions. Yield: 0.80 g.

Loss on drying (determined by TGA): 13.2%.
Assay of water (KF): 6.6%.
Molar ratio among olanzapine/acetonitrile/methylene chloride/water (confirmed by $^1$H NMR analysis) is 1:½:⅙:1.

2-Propanol Solvate of Olanzapine

Example 8

10.0 g of 2-methyl-4-(4-methyl-1-piperazinyl)-10H-thieno[2,3-b][1,5]benzodiazepine ("olanzapine") was suspended in an mixture of 2-propanol (30 ml) and tetrahydrofuran (30 ml). The suspension was heated to 56° C. to obtain a clear solution. Approximately half of the solvent was evaporated under vacuum at 35° C. The resulting solution was cooled to 0° C., and the product was recovered by vacuum filtration and dried under ambient conditions for 12 hours. Yield: 8.9 g.

Loss on drying (determined by TGA): 9.1%.
Molar ratio among olanzapine/2-propanol (confirmed by $^1$H NMR analysis) is 1:½.

Methylene Chloride Solvates IA and IB of Olanzapine

Example 9

10.0 g of 2-methyl-4-(4-methyl-1-piperazinyl)-10H-thieno[2,3-b][1,5]benzodiazepine ("olanzapine") was suspended in methylene chloride (50 ml), and the suspension was heated to 40° C. to obtain a clear solution. The solution was cooled to 0-5° C. and stirred for 15 minutes. The product was isolated by vacuum filtration and dried under ambient conditions. Yield: 11.8 g.

Form IA is obtained.
Loss on drying (determined by TGA): 10.2%.
Molar ratio among olanzapine/methylene chloride (confirmed by $^1$H NMR analysis) is 1:½.

Example 10

5.0 g of 2-methyl-4-(4-methyl-1-piperazinyl)-10H-thieno[2,3-b][1,5]benzodiazepine ("olanzapine") was suspended in methylene chloride (25 ml), and the suspension was heated to 40° C. to obtain a clear solution. The solution was filtered hot and the filtrate was stirred under vacuum for 10 minutes and cooled to 0-5° C. The product was isolated by vacuum filtration and dried under ambient conditions. Yield: 5.33 g.

Form IA is obtained.

Example 11

5.0 g of 2-methyl-4-(4-methyl-1-piperazinyl)-10H-thieno[2,3-b][1,5]benzodiazepine ("olanzapine") was suspended in methylene chloride (25 ml). The suspension was heated to 40° C. to obtain a clear solution. The solvent was evaporated under vacuum at 35° C. to dryness. Yield: 5.5g.

Form IB is obtained.

Loss on drying (determined by TGA): 4.5%.

Molar ratio among olanzapine/methylene chloride (confirmed by $^1$H NMR analysis) is 1:⅙.

Example 12

5.0 g of 2-methyl-4-(4-methyl-1-piperazinyl)-10H-thieno[2,3-b][1,5]benzodiazepine was suspended in methylene chloride (25 ml). The suspension was heated to 40° C. to obtain a clear solution. The solvent was allowed to evaporate under air within two days. Yield: 5.3g.

Form IB is obtained.

Preparation of Form I of Olanzapine

Olanzapine starting materials: anhydrous polymorphic forms or 2-propanol, methylene chloride or acetonitrile solvates of olanzapine.

Example 13

300.0 g of 2-methyl-4-(4-methyl-1-piperazinyl)-10H-thieno[2,3-b][1,5]benzodiazepine ("olanzapine") was suspended in a mixture of tetrahydrofuran (900 ml) and 2-propanol (900 ml). The suspension was then heated to 50-55° C. to obtain a clear solution. Approximately 450 ml of the solvent was evaporated under vacuum at 30-35° C., and the resulting solution was seeded with crystals of form I of olanzapine. Further solvent was removed by with vacuum distillation at this temperature to ½ of the original volume. The product was recovered by filtration and dried at 50° C. and shown to be form I of olanzapine (286.7 g).

Example 14

10.0 g of 2-methyl-4-(4-methyl-1-piperazinyl)-10H-thieno[2,3-b][1,5]benzodiazepine ("olanzapine") was suspended in 2-propanol (30 ml) and heated to 50° C. To this mixture methylene chloride (20 ml) was added to obtain a clear solution. Approximately half of the solvent was evaporated under vacuum at 30-35° C., and then the solution was seeded with crystals of form I of olanzapine and evaporation at this temperature was continued. The product was recovered by filtration and dried at 60° C. and shown to be form I of olanzapine (7.6 g).

Example 15

10.0 g of 2-methyl-4-(4-methyl-1-piperazinyl)-10H-thieno[2,3-b][1,5]benzodiazepine ("olanzapine") was suspended in 2-propanol (30 ml). This suspension was heated to 50° C. and acetone (45 ml) was added to obtain a clear solution. Approximately half of the solvent was evaporated under vacuum at 30-35° C., and then the solution was seeded with the crystals of form I of olanzapine and vacuum distillation at this temperature was continued for further 15 minutes. The product was recovered by filtration and dried at 60° C. to obtain form I of olanzapine (7.2 g).

Example 16

1.0 g of methylene chloride solvate of olanzapine was suspended in 2-propanol (3 ml). The suspension was stirred at room temperature for one hour. The product was filtered and dried in vacuo at 50° C. Yield: 0.86 g.

The invention claimed is:

1. Acetonitrile/methylene chloride/water mixed solvate of olanzapine characterized by an x-ray powder diffraction pattern (2 theta) as follows:
    8.76, 19.39, 20.12.

2. Acetonitrile/methylene chloride/water mixed solvate of olanzapine according to claim 1, characterized by an x-ray powder diffraction pattern (2 theta) as follows:
    8.76, 18.29, 19.39, 19.66, 20.12, 23.13, 23.62, 25.08.

3. Acetonitrile/water mixed solvate of olanzapine characterized by an x-ray powder diffraction pattern (2 theta) as follows:
    8.76, 9.10, 14.05, 19.37, 20.10, 24.55, 25.92, 27.96.

4. Acetonitrile/water mixed solvate of olanzapine according to claim 3, characterized by an x-ray powder diffraction pattern (2 theta) as follows:
    8.76, 9.10, 14.05, 14.44, 18.30, 18.67, 18.84, 19.37, 19.68, 20.10, 20.54, 21.65, 22.79, 23.12, 23.62, 24.55, 25.06, 25.92, 27.96, 28.44.

5. 2-propanol solvate of olanzapine characterized by an x-ray powder diffraction pattern as follows:
    8.74, 14.05, 19.38, 22.65, 23.03, 24.46, 25.92, 28.36.

6. 2-propanol solvate of olanzapine according to claim 5, characterized by an x-ray powder diffraction pattern as follows:
    8.74, 14.05, 14.41, 17.77, 18.22, 18.76, 19.38, 19.81, 19.95, 20.54. 20,96, 21.64, 22.26, 22.65, 23.03, 23.58, 23.90, 24.46, 25.03, 25.39, 25.92, 26.63, 27.47, 27.95, 28.36.

7. Methylene chloride solvate IA of olanzapine characterized by an x-ray powder diffraction pattern as follows:
    10.80, 14.25, 19.22, 22.78, 24.53.

8. Methylene chloride solvate IA of olanzapine according to claim 7, characterized by an x-ray powder diffraction pattern as follows:
    8.85, 10.80, 12.89, 14.09, 14.25, 18.37, 18.81, 19.22, 19.41, 19.57, 20.07, 20.80, 21.00, 21.71, 22.06, 22.25, 22.78, 23.14, 23.62, 24.03, 24.53, 25.04, 25.43, 26.67, 27.51, 28.00, 28.45, 28.70.

9. Methylene chloride solvate IB of olanzapine characterized by an x-ray powder diffraction pattern as follows:
    9.30, 10.80, 14.25, 14.98, 15.94, 19.23, 20.04.

10. Methylene chloride solvate IB of olanzapine according to claim 9, characterized by an x-ray powder diffraction pattern as follows:
    8.43, 8.86, 9.30, 10.80, 14.25, 14.98, 15.94, 16.88, 17.79, 18.40, 18.57, 18.83, 19.23, 19.57, 20.04, 20.79, 21.01, 21.68, 22.06, 22.23, 23.57, 24.02, 24.89, 25.12, 25.46, 26.38, 26.56, 27.50, 28.06, 28.71, 29.02.

11. Process for preparing anhydrous forms of olanzapine by drying at least one solvate according to claim 1.

12. Process wherein the anhydrous form I of olanzapine is prepared by drying at least one solvate according to claim 7.

13. Form A of olanzapine characterized by an x-ray powder diffraction pattern as follows:
11.52, 12.00, 13.35, 13.56, 14.21, 15.47, 16.69, 19.16, 20.25 20.69, 22.12, 24.33, 26.88, 27.13.

14. Form A of olanzapine according to claim 13, characterized by an x-ray powder diffraction pattern as follows:
11.52, 11.83, 12.00, 13.35, 13.56, 14.21, 15.47, 16.69, 17.83, 19.16, 20.25, 20.69, 21.65, 22.12, 23.21, 24.33, 26.88, 27.13, 28.57.

15. Form A of olanzapine according to claim 13, which is in essential pure form.

16. Form A of olanzapine according to claim 13, which is anhydrous.

17. Process for preparing form A of olanzapine as defined in claim 13, comprising the steps of dissolving any form of olanzapine in a mixture of acetonitrile with a solvent in which olanzapine is soluble or in a solvent in which olanzapine is soluble, heating the mixture to obtain a clear solution, optionally filtering the solution, partly evaporating the solvent and isolating the product.

18. Pharmaceutical composition in solid state which comprises form A of olanzapine according to claim 13.

19. Process for preparing anhydrous forms of olanzapine by drying at least one solvate according to claim 3.

20. Process for preparing anhydrous forms of olanzapine by drying at least one solvate according to claim 5.

21. Process for preparing anhydrous forms of olanzapine by drying at least one solvate according to claim 7.

22. Process for preparing anhydrous forms of olanzapine by drying at least one solvate according to claim 9.

23. Process wherein the anhydrous form I of olanzapine is prepared by drying at least one solvate according to claim 9.

* * * * *